United States Patent
Frigg

[11] Patent Number: 5,261,912
[45] Date of Patent: Nov. 16, 1993

[54] IMPLANT FOR AN OSTEOSYNTHESIS DEVICE, IN PARTICULAR FOR SPINAL COLUMN CORRECTION

[75] Inventor: Robert Frigg, Davos-Dorf, Switzerland

[73] Assignee: Synthes (U.S.A.), Paoli, Pa.

[21] Appl. No.: 772,378

[22] PCT Filed: Aug. 15, 1991

[86] PCT No.: PCT/CH91/00174

§ 371 Date: Nov. 13, 1991

§ 102(e) Date: Nov. 13, 1991

[87] PCT Pub. No.: WO92/03100

PCT Pub. Date: Mar. 5, 1992

[30] Foreign Application Priority Data

Aug. 21, 1990 [CH] Switzerland ............ 2705/90

[51] Int. Cl.⁵ ............................................. A61B 17/56
[52] U.S. Cl. ................................... 606/61; 606/72
[58] Field of Search ................ 606/61, 62, 60, 72, 606/73, 74, 75, 59; 411/385; 403/347, 362

[56] References Cited

U.S. PATENT DOCUMENTS

| | | |
|---|---|---|
| 4,611,580 | 9/1986 | Wu ............................ 606/61 |
| 4,641,636 | 2/1987 | Cotrel ........................ 606/61 |
| 4,658,809 | 4/1987 | Ulrich ........................ 606/61 |
| 4,776,328 | 10/1988 | Frey ........................... 606/72 |
| 4,790,297 | 12/1988 | Lugue ........................ 606/61 |
| 4,805,602 | 2/1979 | Puno .......................... 606/61 |
| 4,887,596 | 12/1989 | Sherman .................... 606/72 |
| 4,946,458 | 8/1990 | Harms ........................ 606/72 |
| 5,092,866 | 3/1992 | Breard ....................... 606/61 |

*Primary Examiner*—Michael A. Brown
*Attorney, Agent, or Firm*—Davis Hoxie Faithfull & Hapgood

[57] ABSTRACT

This implant for an osteosynthesis device, in particular for spinal column correction, contains a lower part (2) to be anchored to the bone and an upper part (3) to be adjustably fixed to a longitudinal bar (4). The upper part (3) contains a channel (6) running from front to back and open on the top, which positions the two side arms (7), threaded on the inside (10), to hold the longitudinal bar (4). In addition, there is a clamp (5) for the longitudinal bar (4), which is comprised of a cap (11) with a coaxial, outer rim (15) to surround the arms (7) and a coaxial inner cylinder (12) introduced between the arms (7); the outer surface of the inner cylinder (12) contains threads (13) which correspond to the inner threads (10) of the upper part (3).

7 Claims, 4 Drawing Sheets

IMPLANT FOR AN OSTEOSYNTHESIS DEVICE, IN PARTICULAR FOR SPINAL COLUMN CORRECTION

The invention refers to an implant for an osteosynthesis device, in particular for spinal column correction.

Various methods and osteosynthesis devices are known for the treatment of injuries to the spinal column.

EP-A1 0 128 058 COTREL describes the known method of anchoring hooks or screws at the back of the spinal column and connecting them with a longitudinal bar.

GB-A2 173 104 WEBB describes a pedicle screw with a slotted head designed to hold a longitudinal bar. The head is threaded on the outside so that the longitudinal bar placed in its slot can be clamped down by means of a screw-on cap and an additional loose holding piece.

FR-A 2 624 720 COTREL also describes a pedicle screw with a threaded head designed to hold a longitudinal bar. In this version of a pedicle screw implant the head is also threaded on the outside. The longitudinal bar is clamped in position primarily by the placement on it of two diametrically opposing edges of the screw-on cap. The screw-on cap, furthermore, contains a central opening, through which an additional pin can be screwed against the longitudinal bar, in theory creating a three-point hold.

Finally, EP-A1 0 348 272 LANOY describes a pedicle screw analogous to FR-A 2 624 720, where the two-armed head, however, is threaded on the inside, and these threads hold a grub screw against the longitudinal bar.

In all of the known state-of-the-art systems the connection of the anchoring elements (hooks or screws) to the longitudinal bar is fraught with severe problems, which have to do less with the mechanical solidity of the connection than the intraoperative manipulation of the connection mechanisms by the surgeon, their adaptability, reliability, and space requirements.

The system under GB-A 2 173 104 WEBB requires an additional loose holding element to clamp the longitudinal bar, complicating its use.

In the system under EP-A1 0 348 272 LANOY, both sides of the head are not secured and are spread apart further by the introduction of the grub screw.

The chief disadvantage of the system under FR-A 2 624 720 COTREL is that the screw-on cap cannot be positioned in a way that it locks itself in place. Nor can screwing in a pin through the screw-on cap prevent the connection with the longitudinal bar from loosening. To the contrary, the forced three-point hold produced thereby becomes overtightened, causing the bracing system to become unstable. A further disadvantage consists of the ring-like placement of the screw-on cap onto the longitudinal bar in this well-known system. This kind of placement is particularly disadvantageous if the longitudinal bar is bowed—as is most often the case. In such cases, the longitudinal bar must be left straight for a distance which at least equals the diameter of the screw-on cap. If this requirement is not met, the screw-on cap either cannot be screwed into place or the slightest bend in the longitudinal bar will cause the screw-on cap to be pinched against the longitudinal bar on one side. This one-sided pinch is extremely dangerous since the screw-on cap comes loose with the slightest tilt of the implant (pedicle screw or hook) and releases the longitudinal bar. This kind of implant tilting, caused by stresses on the patient's spinal column, is often observed.

Finally, the system under FR-A 2 624 720 COTREL exhibits a further disadvantage in intraoperative manipulation, namely that the outside threads, onto which the screw-on cap must be placed, are interrupted by the arms. If the screw-on cap is not placed on the implant absolutely coaxially, it becomes tilted during installation. This kind of tilt, because of the requirement of ring-like placement with this system, leads, in turn, to insufficient fixation, which the surgeon fails to notice because the opening in the body limits his view.

This is where the invention seeks to help. The invention seeks to provide an implant for an osteosynthesis device, in particular for spinal column correction, which is easy to use, can be installed securely, and saves space.

Because of the special design of the clamp (cap with a coaxial, outer rim surrounding the arms and a coaxial, threaded inner cylinder to be screwed into place between the arms), the implant under this invention ensures that the longitudinal bar fixed by the clamp locks itself in place. The inner cylinder in the clamp spreads the two arms apart only negligibly when tightened; this spread is simultaneously limited by the outer rim, thus leading to a secure hold between the arm and the clamp. Despite the minuscule dimensions of the device, it can thereby prevent the arms from uncontrollably spreading or angling apart. Thus, the device prevents the clamp, and therefore the longitudinal bar, from accidentally coming loose.

The clamping mechanism, which is centrally located in the implant under this invention, makes it possible to introduce the clamp—guided by its coaxial, threaded inner cylinder—into the threads of the implant head without risking its being pinched.

In particular, by using the implant under this invention with a threaded longitudinal bar, the surgeon can correct the deformation of the spinal column in two steps, which substantially simplifies the surgical operation. In the first step, the spinal column can be corrected axially (by traction or compression). Once this is done, the individual fixating elements (pedicle screws or hooks) are provisionally tightened somewhat in place. This light tightening wedges the threads of the longitudinal bar against the head of the fixating element, which produces a 100% axial fixation of the implant under this invention to the longitudinal bar. In a second step, the derotation can be carried out. Here, the lightly tightened fixating elements function like nuts on a bolt, i.e. the longitudinal bar can be turned with little effort and in an incremental manner around its longitudinal axis without changing the axial correction of the spinal column. After successful derotation of the spinal column, the individual fixating elements can be permanently tightened.

This effect can be strengthened further by also threading the inside of the slotted head of the implant designed to hold the longitudinal bar.

Instead of threaded longitudinal bars and the corresponding threaded insides of the implant head, horizontally ridged or other patterned surfaces may be used.

The preferred use of patterned surfaces in the implant under this invention produces the following additional advantages:

the combination of threaded or horizontally ridged longitudinal bars with similarly patterned receptacles in the implant head provides optimal connection between the two parts;

thanks to the patterned surface of the connecting elements, the so-called derotation (rotation of the bowed longitudinal bar) can be performed independently of any traction or compression;

the holding force of the connection thus achieved is not due merely to friction, but is guaranteed because the patterned surfaces hook into each other.

In a preferred configuration of the invention the inner cylinder of the clamp is pointed on its free end to achieve a clear fixation on a point. Because of the centrally located point even relatively severely bowed longitudinal bars can be fixed securely. Contrary to known implant systems, which also contain a point, the point on the implant under this invention serves only to press the longitudinal bar (preferably with a patterned surface) into the lower portion of the channel formed by the two arms. This fixes the pedicle screw and/or hooks axially to the longitudinal bar. Rotating the longitudinal bar in the pedicle screw head, on the other hand, is of lesser importance since two pedicle screws are used per vertebra and, furthermore, the two longitudinal bars are also connected to each other.

In another preferred configuration, the outer threads of the inner cylinder of the clamp do not cover the entire surface of the exterior, resulting in an unthreaded front portion. The diameter of the smooth shoulder thus formed corresponds to the interior diameter of the inner threads of the implant head. The length of the shoulder should be such that it centers the clamp as it is being installed and guides it along the longitudinal axis of the threads. This prevents the clamp from being tilted during installation. This guidance function is of great importance for all implant systems with interrupted threads, i.e. a slotted implant head, including the implant under this invention.

Various configurations of the invention, which also explain the principle behind their function, are presented in the figures and are described in greater detail below.

The invention is presented in the figures in various configurations, where the bone-side portion of the implant consists of a pedicle screw. However, other implant elements for anchoring the device to the bone, in particular the vertebrae, are suitable for this invention, e.g. hooks with slotted heads.

FIG. 1 presents an axial cross-section through the bone-side portion of the implant under this invention in the form of a pedicle screw;

FIG. 2 shows a top view of the implant element of FIG. 1 with the longitudinal bar introduced, but not yet fixed;

FIG. 3 presents an axial cross-section of the clamp in the implant under this invention;

Figure 3:
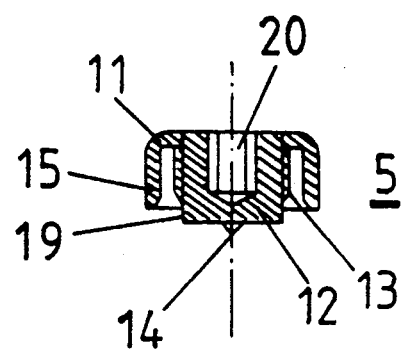
Figure 4:
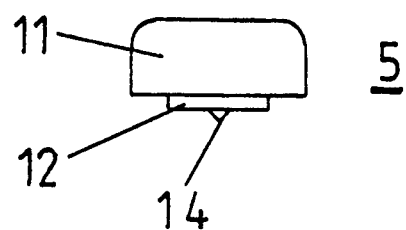
FIG. 4 shows a side view of the clamp in FIG. 3.
Figure 5:
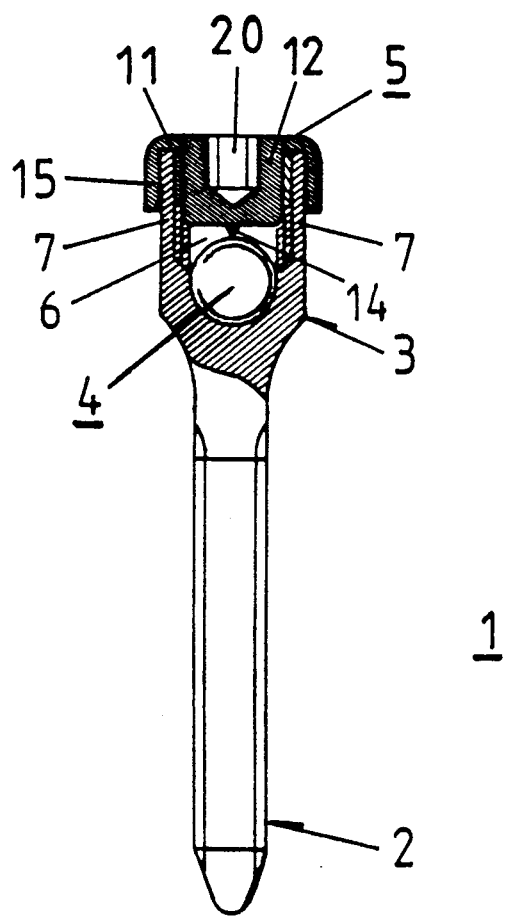
FIG. 5 shows a longitudinal cross-section of the implant under this invention with a fixed longitudinal bar.

The implant shown in FIGS. 1 through 4 in its parts and in FIG. 5 as a whole primarily consists of a pedicle screw 1 with a lower part 2, which is threaded (not shown), to anchor the bone and an upper part 3, designed as a screw head, for loose fixation to a longitudinal bar 4 and a clamp 5.

The upper part 3 has a channel 6 running from front to back which is open on top and positions the two lateral arms 7 to hold the longitudinal bar 4. The portion 8 of the channel 6 closest to the lower part 2 has a patterned surface in order to improve the hold with the threads 18 of the longitudinal bar 4. The lateral inner flanks 9 of the arms 7 are threaded on the inside 10.

The clamp 5 shown in FIGS. 3 and 4 consists primarily of a cap 11 with rim 15 and an inner cylinder 12 integral with and extending inwardly from the rim 15 forming a space there between; the outer surface of the inner cylinder 12 has threads 13 to correspond with the inner threads 10 of the screw head 3. At its free end the inner cylinder 12 also contains a point 14. The clamp 5 contains a hexagonal opening 20 centrally located in the cap 11 and in the inner cylinder 12 to permit assembly using a suitable tool (Allen wrench).

Figure 1:
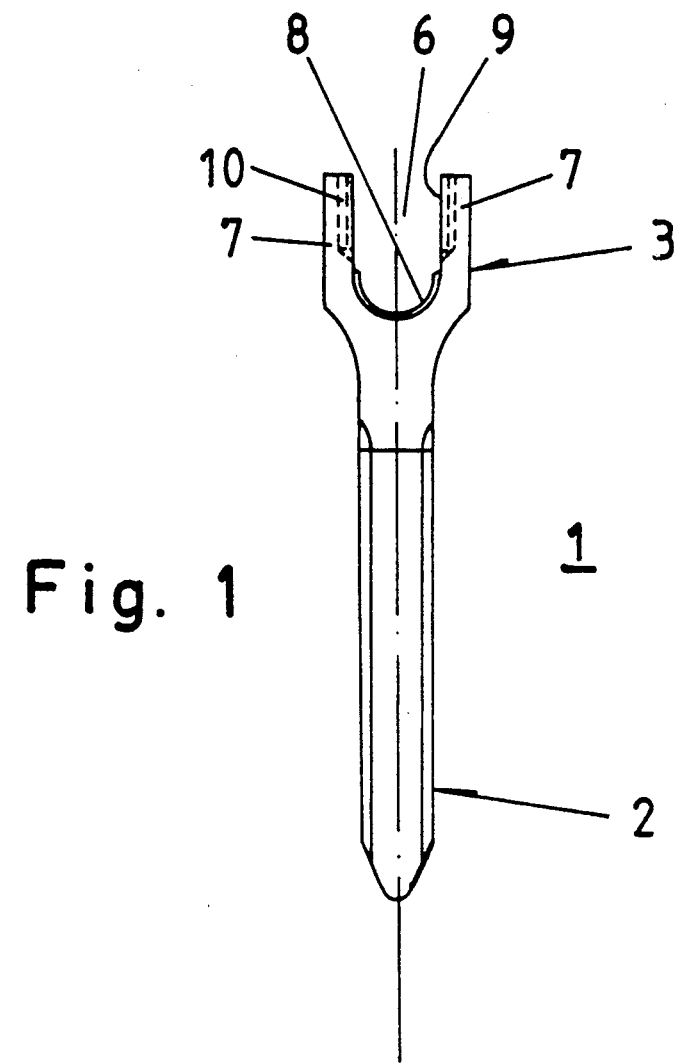
Figure 2:
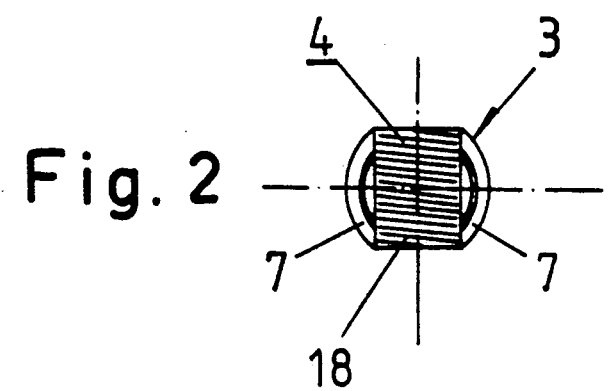

As a rule, the implant is positioned so that pedicle screw 1 is anchored in the bone with its lower threaded portion 2; the longitudinal bar 4—as shown in FIG. 2—is introduced into it from above between the two arms 7 (with inner threads 10) of the pedicle screw head 3.

The clamp 5, described in detail in FIGS. 3 and 4, is then mounted on the pedicle screw head 3, as shown in FIG. 5. The diameter of the unthreaded front portion 19 at the free end of the inner cylinder 12 corresponds to the diameter of the inner threads 10 and is long enough to guarantee that the clamp 5 is securely centered during installation until the outer threads 13 of the inner cylinder 12 interlock with the inner threads 10 in a precisely coaxial direction. Finally, as the clamp 5 is screwed in, the point 14 of the clamp 5 comes to rest against the longitudinal bar 4, which fixes the latter both axially and rotationally. At the same time, the rim 15 of the cap 11 secures the two arms 7 of the pedicle screw head 3.

Figure 6:
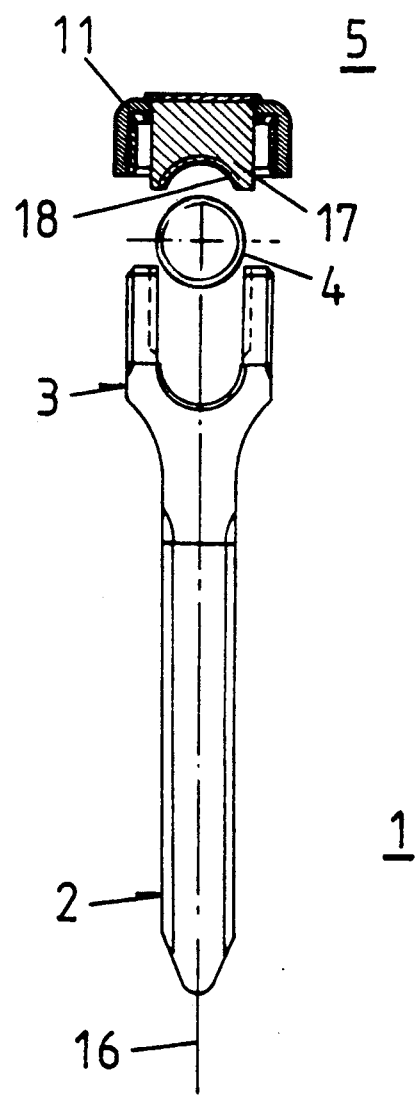
FIG. 6 shows a longitudinal cross-section of the implant under this invention in FIG. 5 with a modified clamp.

FIG. 6 shows a second configuration of the invention, where the clamp 5—instead of an inner cylinder with a point firmly connected with the cap 11—has a circular cylinder 17 which can be rotated around the implant axis 16 and has a concave free surface 18. The geometry of the concavity 18 is specifically designed to correspond to the circular surface of the longitudinal bar 4. In all other ways, the clamp 5 is structured as in the configuration in FIG. 5.

When this modified clamp 5 is screwed on, the concave surface 18 of the circular cylinder 17 comes to rest against the corresponding convex cylindrical outer surface of the longitudinal bar 4 located between the arms 7. Once the clamp 5 is almost completely screwed on, the circular cylinder 17 is prevented from rotating so that only the rotatable cap 11 can move around the implant axis 16. Once the clamp 5 is completely screwed on, a fixation area is created that covers the entire surface 18, a quite significant improvement over the single point 14 fixation in FIG. 5.

I claim:

1. Implant for an osteosynthesis device, in particular for spinal column correction, with a lower part (2) to be anchored to the bone and an upper part (3) to be adjustably fixed to a longitudinal bar (4); the upper part (3) contains a channel (6) running from front to back and open on top, which positions the two side arms (7), threaded on the inside (10), to hold the longitudinal bar (4), characterized in that it has a clamp (5) for the longitudinal bar (4) comprising a cap (11) with a coaxial, outer rim (15) to surround the arms (7) and a coaxial inner cylinder (12) integral with and extending inwardly from said rim forming a space there between, said inner cylinder to be introduced between the arms (7); the outer surface of the inner cylinder (12) has threads (13) which correspond to the inner threads (10) of the upper part (3).

2. Implant according to claim 1, characterized in that the portion (8) of the channel (6) facing the lower part (2) contains a patterned surface.

3. Implant according to claim 1, characterized in that the inner cylinder (12) of the clamp (5) contains a point (14) preferably located in the center of its free end.

4. Implant according to claim 1, characterized in that the outer threads (13) of the coaxial inner cylinder (12) do not run completely to the latter's free end resulting in an unthreaded front portion (19) of the inner cylinder (12).

5. Implant according to claim 1, characterized in that the inner cylinder (12) of the clamp (5) is structured as a circular cylinder (17) which can be turned around the implant axis (16) and has a concave free surface (18).

6. Implant according to claim 5, characterized in that the concave surface (18) matches the cylindrical surface of the longitudinal bar (4).

7. Use of the implant according to claim 1 to fix the longitudinal bar (4) in an adjustable manner, characterized in that the longitudinal bar (4) is threaded (18).

* * * * *